(12) United States Patent
Sakai

(10) Patent No.: US 9,828,488 B2
(45) Date of Patent: Nov. 28, 2017

(54) POLYVINYL CHLORIDE RESIN COMPOSITION

(71) Applicant: RIKEN TECHNOS CORPORATION, Tokyo (JP)

(72) Inventor: Koji Sakai, Tokyo (JP)

(73) Assignee: RIKEN TECHNOS CORPORATION, Tokyo (JP)

(*) Notice: Subject to any disclaimer, the term of this patent is extended or adjusted under 35 U.S.C. 154(b) by 0 days.

(21) Appl. No.: 15/227,038

(22) Filed: Aug. 3, 2016

(65) Prior Publication Data

US 2016/0355666 A1    Dec. 8, 2016

Related U.S. Application Data

(63) Continuation of application No. 14/240,528, filed as application No. PCT/JP2012/071434 on Aug. 24, 2012, now abandoned.

(30) Foreign Application Priority Data

Aug. 31, 2011   (JP) .................................. 2011-189494
Aug. 22, 2012   (JP) .................................. 2012-182880

(51) Int. Cl.

| | |
|---|---|
| *C08K 5/12* | (2006.01) |
| *A61L 31/14* | (2006.01) |
| *A61L 29/04* | (2006.01) |
| *A61L 31/04* | (2006.01) |
| *A61L 29/14* | (2006.01) |
| *C08K 5/00* | (2006.01) |
| *C08K 5/04* | (2006.01) |
| *C08K 5/1515* | (2006.01) |
| *A61J 1/10* | (2006.01) |
| *A61L 29/12* | (2006.01) |
| *C08L 27/06* | (2006.01) |
| *B29K 27/06* | (2006.01) |
| *C08L 91/00* | (2006.01) |

(52) U.S. Cl.
CPC  *C08K 5/12* (2013.01); *A61J 1/10* (2013.01); *A61L 29/04* (2013.01); *A61L 29/041* (2013.01); *A61L 29/126* (2013.01); *A61L 29/141* (2013.01); *A61L 29/143* (2013.01); *A61L 31/04* (2013.01); *A61L 31/048* (2013.01); *A61L 31/141* (2013.01); *A61L 31/143* (2013.01); *C08K 5/005* (2013.01); *C08K 5/0016* (2013.01); *C08K 5/04* (2013.01); *C08K 5/1515* (2013.01); *C08L 27/06* (2013.01); *B29K 2027/06* (2013.01); *C08L 91/00* (2013.01); *Y10T 428/139* (2015.01); *Y10T 428/1334* (2015.01); *Y10T 428/1352* (2015.01); *Y10T 428/1393* (2015.01); *Y10T 428/1397* (2015.01)

(58) Field of Classification Search
CPC ...... A61L 29/04; A61L 29/141; A61L 29/143; A61L 31/04; A61L 31/141; A61L 31/143; A61J 1/10; C08L 27/06; C08K 5/12; C08K 5/005; C08K 5/1515; C08K 5/0016; B29K 2027/06; Y10T 428/1334; Y10T 428/1352; Y10T 428/139; Y10T 428/1393; Y10T 428/1397
USPC .................................................... 264/331.15
See application file for complete search history.

(56) References Cited

U.S. PATENT DOCUMENTS

| | | | | |
|---|---|---|---|---|
| 4,507,123 A | * | 3/1985 | Yoshida | A61J 1/10 604/408 |
| 4,657,541 A | * | 4/1987 | Ichikawa | A61J 1/10 128/DIG. 24 |
| 7,964,658 B2 | * | 6/2011 | Grass | C07C 29/141 524/287 |
| 2003/0014948 A1 | | 1/2003 | Gott et al. | |
| 2007/0037926 A1 | | 2/2007 | Olsen et al. | |
| 2008/0132712 A1 | * | 6/2008 | Denoux | C07C 57/12 549/219 |
| 2011/0281987 A1 | * | 11/2011 | Godwin | C08K 5/0016 524/291 |

FOREIGN PATENT DOCUMENTS

| | | |
|---|---|---|
| JP | 5933343 A | 2/1984 |
| JP | 6375050 A | 4/1988 |
| JP | 824329 A | 1/1996 |
| JP | 2003226788 A | 8/2003 |
| JP | 2003253072 A | 9/2003 |
| JP | 2005517045 A | 6/2005 |
| JP | 2009504851 A | 2/2009 |

* cited by examiner

*Primary Examiner* — Walter B Aughenbaugh
(74) *Attorney, Agent, or Firm* — Karl F. Milde, Jr.; Eckert Seamans Cherin & Mellott, LLC

(57) ABSTRACT

PURPOSE: The present invention provides a polyvinyl chloride resin composition which is superior in heat stability and processability and has less elution from the composition.
CONSTITUTION: a polyvinyl chloride resin composition comprising 100 parts by weight of a polyvinyl chloride resin, 10 to 120 parts by weight of di(2-ethylhexyl)terephthalate, and 0.5 to 20 parts by weight of epoxidized vegetable oil having a peroxide number of 5 or less.

3 Claims, No Drawings

POLYVINYL CHLORIDE RESIN COMPOSITION

This patent application is a continuation of the U.S. patent application Ser. No. 14/240,528, filed Feb. 24, 2014, which, in turn is a U.S. National Stage filing of co-pending PCT Patent Application No. PCT/JP2012/071434, filed Aug. 24, 2012, which, in turn, is based upon and claims the benefit of Japanese Patent Application No. 2011-189494, filed Aug. 31, 2011, and Japanese Patent Application No. 2012-182880, filed Aug. 22, 2012, each application of which is incorporated herein in its entirety.

FIELD OF THE INVENTION

The present invention relates to a polyvinyl chloride resin composition, particularly, a polyvinyl chloride resin composition which is superior in heat stability and processability and has less elution from the composition and, therefore, is suitable for medical instruments such as medical tubes and medical bags.

BACKGROUND OF THE INVENTION

Polyvinyl chloride resin compositions comprising a polyvinyl chloride resin together with a plasticizer have widely been used as a material for medical instruments such as, for example, medical tubes such as catheters, and medical bags such as blood bags, liquid medicine bags and drainage bags, because flexibility of the composition may be adjusted over a wide range by varying an amount of the plasticizer, and the composition has good moldability, adhesion, processability, heat resistance and kink resistance and is less costly. However, when a molded article composed of a polyvinyl chloride resin composition comprising a plasticizer is brought into contact with body fluids such as blood or with various aqueous solutions, the plasticizer or other additives may elute.

In general, a resin composition for medical instruments is desired not to cause elution of additives such as a plasticizer. Further, the resin composition for medical instruments is desired to be heat stable, because the medical instruments are necessarily sterilized.

Various methods have been proposed foe reducing the elution. For example, it is known to add a specific silicone oil to a polyvinyl chloride resin composition comprising di(2-ethylhexyl)phthalate (DOP) as a plasticizer (see the following Patent Literature 1). It is also proposed to add epoxidized vegetable oil hewing a peroxide number of 10 or less to a polyvinyl chloride resin composition comprising the DOP as a plasticizer (see the following Patent Literature 2). However, in reality, epoxidized vegetable oils having peroxide numbers of 5 or more only are described and reduction of the elution is not enough.

Also, it is proposed to substitute bis(2-ethylhexyl)terephthalate (DOTP) for the conventional DOP as a plasticizer to be added to a polyvinyl chloride resin (see the following Patent Literatures 3 to 5). These Patent Literatures do not refer to application of the polyvinyl chloride resin compositions to medical instruments or on reduction of elution. Further, these polyvinyl chloride resin compositions are inferior in heat stability and processability.

PRIOR ART LITERATURES

Patent Literatures

Patent Literature 1: Japanese Patent Application Laid-Open No. Sho 59-33343/1984
Patent Literature 2: Japanese Patent Application Laid-Open No. Hei 8-24329/1996
Patent Literature 3: Japanese Patent Application Laid-Open No. 2003-226788
Patent Literature 4: Japanese Patent Application Laid-Open No. 2003-253072
Patent Literature 5: Japanese Patent Application Laid-Open No. Sho 63-75050/1988

SUMMARY OF THE INVENTION

Purpose of the Invention

The present invention has been made in view of the aforesaid circumstances. An object of the present invention is to provide a polyvinyl chloride resin composition which is superior in heat stability and processability and has less elution.

Means for Achieving the Purpose

The present inventor has found that the aforesaid purpose is achieved by adding di(2-ethylhexyl)terephthalate as a plasticizer together with epoxidized vegetable oil having a peroxide number of 5 or less to polyvinyl chloride resin.

Thus, the present invention is a polyvinyl chloride resin composition comprising 100 parts by weight of a polyvinyl chloride resin, 10 to 120 parts by weight of di(2-ethylhexyl)terephthalate, and 0.5 to 20 parts by weight of epoxidized vegetable oil having a peroxide number of 5 or less. The present invention also provides a medical instrument composed of the polyvinyl chloride resin composition.

Effects of the Invention

The present polyvinyl chloride resin composition is superior in heat stability and processability and has less elution from the composition and, therefore, is suitably used for medical instruments such as medical tubes and medical bags.

EMBODIMENTS OF THE INVENTION

The present polyvinyl chloride resin composition will be described in detail below. The present polyvinyl chloride resin composition comprises polyvinyl chloride resin, di(2-ethylhexyl)terephthalate as a plasticizer and epoxidized vegetable oil having a peroxide number of 5 or less.

The polyvinyl chloride resin encompasses any polymer having the group, —$CH_2$—CHCl—, and includes homopolymers of vinyl chloride, copolymers of vinyl chloride with any other polymerizable monomer except vinyl acetate, such as ethylene-vinyl chloride copolymers, modified homopolymers or copolymers, such as post-chlorinated vinyl chloride copolymer, and chlorinated polyolefins having a structure similar to that of the aforesaid polyvinyl chloride resin, such as chlorinated polyethylene.

The polyvinyl chloride resin preferably has a number average degree of polymerization of 300 to 7000, mere preferably 500 to 3000. The polyvinyl chloride resin in the present polyvinyl chloride resin composition may be used alone or in a combination of two or more of these resins.

Di(2-ethylhexyl)terephthalate used as a plasticizer in the present invention is represented by the following formula, where two 2-ethylhexyloxycarbonyl groups are present at the para position to each other and, therefore, is different from di(2-ethylhexyl)phthalate (DOP) where two 2-ethylhexyloxycarbonyl groups are present at the ortho position to each other.

[Compound 1]

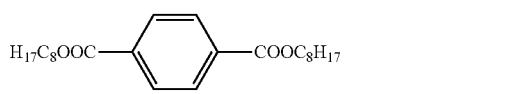

Di(2-ethylhexyl)terephthalate is commercially available.

The amount of di(2-ethylhexyl) terephthalate is 30 to 120 parts by weight, preferably 10 to 100 parts by weight, more preferably 20 to 80 parts by weight, still more preferably 20 to 65 parts by weight, per 100 parts by weight of the polyvinyl chloride resin. If the amount is less than the lower limit, flexibility of the composition may not be enough. If the amount exceeds the upper limit, strength of the composition may markedly decrease or bleeding may occur.

The present resin composition comprises di(2-ethylhexyl) terephthalate as a plasticizer and, therefore, shows less elution. Particularly, the present resin composition attains the following effect. In a pH test described below, where a sheet composed of the present resin composition is immersed in distilled water, change in a pH of the distilled water is very low. This means that a less amount of materials which affects the pH elute. Accordingly, medical instruments made of this resin composition can be used in contact with medicaments which are prone to be affected by a pH.

The present polyvinyl chloride resin composition further comprises epoxidized vegetable oil. The epoxidized vegetable oil used in the present invention is prepared in a known method by epoxidizing naturally-occurring vegetable oil with hydrogen peroxide or an organic peroxy acid such as acetic peroxide and has a peroxide number of 5 or less, preferably 4 or less, more preferably 3 or less. If the number exceeds 5, the effect of reducing an amount of eluted materials is not enough.

The epoxidized vegetable oil is commercially available or may be prepared, for example, in the following manner. Vegetable oil is oxidized with an organic peroxy acid as an oxidant to obtain epoxidized vegetable oil having a peroxide number of 20 to 40. This is then heated under a reduced pressure to obtain epoxidized vegetable oil having a peroxide number of 5 or less. The heating temperature is usually 120 to 250 degrees C., preferably 130 to 200 degrees C. The heating time is several minutes to several hours. As the heating time is longer, a lower peroxide number is obtained, one hour or longer is preferred. If the temperature is lower than 120 degrees C., a longer heating time is necessary. If the temperature exceeds 250 degrees C., side-reactions such as polymerization of epoxy groups may occur.

Examples of the vegetable oil for the epoxidized vegetable oil include soybean oil, linseed oil and rapeseed oil. Soybean oil is particularly preferred.

Potassium iodide is added to a sample and an amount of iodine liberated from the sample, expressed in meq/kg of sample, is the peroxide number according to the method described in "The Standard Methods for the Analysis of Fats, Oils and Related Materials", Japan Oil Chemists' Society (ed.), Asakura Publishing Co., Ltd., 1966. A higher peroxide number means that a sample contains sore peroxide groups.

The amount of the epoxidized vegetable oil is 0.5 to 20 pares by weight, preferably 1 to 12 parts by weight, more preferably 3 to 7 parts by weight, per 100 parts by weight of the polyvinyl chloride resin. If the amount is less than the lower limit, heat stability of the composition may not be enough and the affect of reducing an amount of eluted materials may not be attained. If the amount exceeds the upper limit, bleeding-out may occur. No incremental effect is attained by the oil over the upper limit.

The present polyvinyl chloride resin composition may further comprise silicone oil. The amount of the silicone oil is 0.05 to 10 parts by weight, preferably 0.3 to 10 parts by weight, per 100 parts by weight of the polyvinyl chloride resin. If the amount is less than the lower limit, the effect of reducing an amount of eluted materials may not be attained. No incremental effect is attained by the silicone oil over the upper limit.

Examples of the silicone oil include polymethylphenylsiloxane, polydimethylsiloxane, poly(methyl hydrogen siloxane), and those modified with an amino group or a carboxyl group.

The present polyvinyl chloride resin composition may further comprise a stabilizer which is generally added in a flexible polyvinyl chloride resin for food or medical applications. Examples of the stabilizer include, for example, barium-zinc type and calcium-zinc typo ones, such as composite stearate of calcium and zinc. The amount of the stabilizer is preferably 0.1 to 10 parts by weight per 100 parts by weight of the polyvinyl chloride resin. If the amount is less than 0.1 part by weight, no effect of the stabilizer is attained. No incremental effect is attained by the stabilizer over the upper limit.

The present polyvinyl chloride resin composition may further comprise additives such as other plasticizers, pigments, dyes, heat stabilizers, antioxidants and lubricants, if necessary.

The present polyvinyl chloride resin composition may be obtained by melt-kneading a polyvinyl chloride resin, di(2-ethylhexyl)terephthalate, epoxidized vegetable oil and, if necessary, optional components in a press kneader at a resin temperature of 150 to 160 degrees C. for 5 to 10 minutes.

The present polyvinyl chloride resin composition is superior in heat stability and shows less elution and, therefore, may suitably be used for various medical instruments such as medical tubes, medical bags and breath masks. The medical tubes include, for example, feeding tubes, hemodialysis tubes, respiratory tubes, catheter, pressure monitor tubes and heparin tubes. The medical bags include blood bags, liquid medicine bags and drainage bags.

In the following, the present invention will be illustrated in core detail by the Examples, but are not limited thereto.

EXAMPLES

Examples 1 to 7 and Comparative Examples 1 to 14

The components in the amounts (part by weight) as shown in Table 1 were melt kneaded in a press kneader approximately at 160 degrees C. to prepare a polyvinyl chloride resin composition. The composition was put through rolls into a sheet. The sheet was formed into a predetermined size by a press machine to obtain a specimen. The specimen was subjected to the following tests (1) and (2). Besides, the polyvinyl chloride resin composition obtained above was subjected to the following test (3). The results are as shown in Table 1.

The abbreviations in the Tables are as follows.
PUC: polyvinyl Chloride resin (average degree of polymerization: 1300)
DOTP: di(2-ethylhexyl)terephthalate
DOP: di(2-ethylhexyl)phthalate
TOTM: tri(2-ethylhexyl)trimellitate
DINCH: diisononylcyclchexane-1,2-dicarboxylate
DOA: di(2-ethylhexyl)adipate Tests
(1) Tests on Eluted Materials The following tests were carried out according to the Japanese Pharmacopoeia. 15.00 Grams of the specimen with a thickness of 1 mm were washed with water and then dried at room temperature. This specimen was put into a 500 ml-volume conical flask, followed by addition, of 300 ml of distilled water. The flask was sealed with a silicone rubber stopper and then heated in a high-pressure steam sterilizer at 121 degrees C. for 60 minutes. After decompression, the conical flask containing the specimen therein was removed from the high-pressure steam sterilizer and allowed to stand until the temperature of the flask decreased to room temperature. The specimen was transferred together with the distilled water in to a 300 ml-volume volumetric flask, to which distilled water was supplemented to a total volume of just 300 ml to obtain a test solution. Separately, the same procedures were repeated to prepare a blank, test solution containing no specimen. The test solution and the blank test solution were subjected to the following tests (i) to (v).
(i) pH Test To each 20 ml of the test solution and the blank test solution, added was 1 ml of a solution which had been prepared by adding water to 1.0 g of potassium chloride to a total amount of 1000 ml. Then, pH values of the resulting solutions were measured and a difference between these pH values was calculated. A larger difference means that a more amount of materials which affect pH elute.
(ii) Tin Test
Preparation of a Test Solution for the Tin Test 10.0 Ml of the test solution was put in a 25 ml volumetric flask, to which a potassium permanganate solution was added dropwise until the color of the solution turned pale red, and then a small amount of L-ascorbic acid was added to cause decoloration. To the solution, added sequentially were 1.5 ml of 1N hydrogen chloride, 5.0 ml of citric acid diluted with water by 10 times, and 2.5 ml of polyvinyl alcohol having a degree of polymerization of 2000, followed by addition of 5.0 ml of a solution of phenylfluoron in ethanol, and water was further added to a total amount of 25.0 ml. The resulting solution was shaken well and then allowed to stand for approximately 20 minutes to obtain a test solution for the tin test.
Preparation of an Aqueous Dilute Nitric Acid Solution Dilute nitric acid was prepared according to the Japanese Phamacopoeia, Sixteenth Edition. That is, water was added to 10.5 ml of nitric acid to a total amount of 100 ml, which was a 10% dilute nitric acid. The 10% dilute nitric acid was further diluted by three times to obtain an aqueous dilute nitric acid solution (A).
Standard Solution for the Tin Test A tin standard solution (1000 ppm, ex. Kanto Chemical Co., Inc.) was diluted to a concentration of 1.0 μg/ml. 5.0 Ml of this was put in a 20 ml stoppered volumetric flask instead of the test solution. A potassium permanganate solution was added dropwise until the color of the solution turned pale red. Then the same procedures as in the aforesaid preparation of a test solution for the tin test were repeated to obtain a standard solution for the tin test (0.25 μg/ml), except that the aqueous dilute nitric acid solution (A) in place of water was added to a total amount of 20 ml. Similarly, standard solutions for the tin test of concentrations of 0.01 μg/ml, 0.05 μg/ml and 0.1 μg/ml were prepared.
Quantitative Analysis of Tin The standard solutions for the tin test were subjected to measurement of an absorbance at a wavelength of 510 nm with a water reference to prepare a calibration curve. Similarly, the test solutions for the tin test were subjected to measurement of absorbances at the same wavelength with a water reference. Concentrations of tin were found from the absorbances on the calibration curve. A polyvinyl chloride resin composition may contain tin derived from a catalyst in the preparation of vinyl chloride or contaminants.
(iii) Tests on Potassium Permanganate-Reducing Materials 20.0 Ml of the test solution was put in a stoppered conical flask, to which 20.0 ml of a 0.002 mol/L potassium permanganate solution and 1 ml of the 10% dilute nitric acid were added, boiled for 3 minutes and cooled. After 0.1 g of potassium iodide was added, the flask was tightly stopped, snaked and allowed to stand for ten minutes, to which five drops of a starch solution were added as an indicator. Titration with a 0.01 mol/L sodium thiosulfate solution was carried out to determine an amount of potassium permanganate solution consumed (X). The same procedures as described above were repeated on the blank test solution to determine an amount of potassium permanganate solution consumed (Y). The value, X−Y, is indicated as $\Delta KMnO_4$. A higher value means that a more amount of potassium permanganate-reducing materials, mainly organic substances, eluted.
(iv) Evaporation Residue Test Twenty ml of the test solution was evaporated to dryness on a water bath. The resulting residue was dried at 105 degrees C. for an hour and then weighed.

(v) Ultraviolet Absorption Spectrum Test

The blank test solution was put in a quartz cell having a liquid thickness of 10 mm and used for correction of a ultraviolet and visible spectrophotometer, U-3010 (ex. Hitachi, Ltd.). Similarly, the test solutions were put in the quartz cell and subjected to measurement of absorbance in the wavelength range of 220 to 350 nm with the same spectrophotometer to determine a maximum absorbance. The results are as shown in Table 1.

(3) Processability Test

Thirty grams of the polyvinyl chloride resin composition were kneaded in LABO PLASTOMILL 30C 150 type, ex Toyo Seiki Seisaku-Sho, Ltd., under the conditions of a cell temperature or 160 degrees C., a rotation speed of 50 rpm and a preheating time of 5 minutes to measure a period of time which is necessary for the composition to reach a maximum torque value. This is referred to as a gelation time. A shorter gelation time means that the processability is better.

TABLE 1

|  | Example 1 | Example 2 | Example 3 | Example 4 | Example 5 | Example 6 | Example 7 | Comp. Ex. 1 | Comp. Ex. 2 | Comp. Ex. 3 | Comp. Ex. 4 |
|---|---|---|---|---|---|---|---|---|---|---|---|
| PVC | 100 | 100 | 100 | 100 | 100 | 100 | 100 | 100 | 100 | 100 | 100 |
| DOTP (molecular weight: 391) | 50 | 10 | 50 | 100 | 50 | 50 | 50 | 50 | 50 | 50 | 50 |
| DOP (molecular weight: 391) | 0 | 0 | 0 | 0 | 0 | 0 | 0 | 0 | 0 | 0 | 0 |
| TOTM (molecular weight: 547) | 0 | 0 | 0 | 0 | 0 | 0 | 0 | 0 | 0 | 0 | 0 |
| DINCH (molecular weight: 424) | 0 | 0 | 0 | 0 | 0 | 0 | 0 | 0 | 0 | 0 | 0 |
| DOA (molecular weight: 371) | 0 | 0 | 0 | 0 | 0 | 0 | 0 | 0 | 0 | 0 | 0 |
| Epoxidized soybean oil (peroxide number: 3) | 1 | 5 | 5 | 5 | 10 | 20 | 5 | 0 | 30 | 0 | 0 |
| Epoxidized soybean oil (peroxide number: 8) | 0 | 0 | 0 | 0 | 0 | 0 | 0 | 0 | 0 | 1 | 5 |
| Ca—Zn type composite stabilizer | 1.2 | 1.2 | 1.2 | 1.2 | 1.2 | 1.2 | 1.2 | 1.2 | 1.2 | 1.2 | 1.2 |
| Silicone oil* | 0 | 0 | 0 | 0 | 0 | 0 | 0.1 | 0 | 0 | 0 | 0 |
| ΔpH | 0.2 | 0.2 | 0.2 | 0.2 | 0.2 | 0.2 | 0.2 | 0.2 | 0.2 | 0.2 | 0.2 |
| Tin, μg/ml | 0.01 | 0.01 | 0.01 | 0.01 | 0.01 | 0.01 | 0.01 | 0.01 | 0.01 | 0.01 | 0.01 |
| ΔKMnO$_4$, ml | 0.1 | 0.1 | 0.1 | 0.1 | 0.1 | 0.1 | 0.1 | 0.1 | 0.1 | 0.1 | 0.1 |
| Evaporation residue, mg | 0.2 | 0.3 | 0.3 | 0.3 | 0.4 | 0.4 | 0.1 | 0.1 | 0.4 | 0.3 | 0.4 |
| Ultraviolet absorption spectrum (absorbance) | 0.03 | 0.04 | 0.04 | 0.03 | 0.04 | 0.05 | 0.01 | 0.02 | 0.05 | 0.03 | 0.06 |
| Heat stability, min. | 95 | 140 | 115 | 95 | 120 | 130 | 115 | 75 | 130 | 95 | 115 |
| Processability (gelation time), minute(') and second(") | 3'12" | 2'42" | 3'00" | 3'46" | 3'12" | 3'23" | 3'02" | 4'20" | 3'24" | 3'17" | 3'06" |

|  | Comp. Ex. 5 | Comp. Ex. 6 | Comp. Ex. 7 | Comp. Ex. 8 | Comp. Ex. 9 | Comp. Ex. 10 | Comp. Ex. 11 | Comp. Ex. 12 | Comp. Ex. 13 | Comp. Ex. 14 |
|---|---|---|---|---|---|---|---|---|---|---|
| PVC | 100 | 100 | 100 | 100 | 100 | 100 | 100 | 100 | 100 | 100 |
| DOTP (molecular weight: 391) | 50 | 50 | 0 | 0 | 0 | 0 | 0 | 0 | 0 | 0 |
| DOP (molecular weight: 391) | 0 | 0 | 50 | 50 | 0 | 0 | 0 | 0 | 0 | 0 |
| TOTM (molecular weight: 547) | 0 | 0 | 0 | 0 | 50 | 50 | 0 | 0 | 0 | 0 |
| DINCH (molecular weight: 424) | 0 | 0 | 0 | 0 | 0 | 0 | 50 | 50 | 0 | 0 |
| DOA (molecular weight: 371) | 0 | 0 | 0 | 0 | 0 | 0 | 0 | 0 | 50 | 50 |
| Epoxidized soybean oil (peroxide number: 3) | 0 | 0 | 5 | 5 | 5 | 5 | 5 | 5 | 5 | 5 |
| Epoxidized soybean oil (peroxide number: 8) | 10 | 20 | 0 | 0 | 0 | 0 | 0 | 0 | 0 | 0 |
| Ca—Zn type composite stabilizer | 1.2 | 1.2 | 1.2 | 1.2 | 1.2 | 1.2 | 1.2 | 1.2 | 1.2 | 1.2 |
| Silicone oil* | 0 | 0 | 0 | 0.1 | 0 | 0.1 | 0 | 0.1 | 0 | 0.1 |
| ΔpH | 0.2 | 0.2 | 0.7 | 0.5 | 0.6 | 0.5 | 0.6 | 0.5 | 0.6 | 0.5 |
| Tin, μg/ml | 0.01 | 0.01 | 0.01 | 0.01 | 0.02 | 0.01 | 0.02 | 0.01 | 0.02 | 0.01 |
| ΔKMnO$_4$, ml | 0.1 | 0.1 | 0.2 | 0.1 | 0.1 | 0.1 | 0.1 | 0.1 | 0.1 | 0.1 |
| Evaporation residue, mg | 0.5 | 0.6 | 0.4 | 0.3 | 0.2 | 0.2 | 0.2 | 0.2 | 0.2 | 0.2 |
| Ultraviolet absorption spectrum (absorbance) | 0.06 | 0.06 | 0.02 | 0.01 | 0.01 | 0.01 | 0.01 | 0.01 | 0.01 | 0.01 |
| Heat stability, min. | 120 | 130 | 155 | 155 | 125 | 125 | 85 | 85 | 85 | 85 |
| Processability (gelation time), minute(') and second(") | 3'17" | 3'28" | 1'10" | 1'10" | 5'26" | 5'26" | 4'38" | 4'38" | 1'02" | 1'03" |

*KF-96 100cs (trade name, dimethyl silicone oil, ex Shin-Etsu Chemical Co., Ltd.)

(2) Heat Stability Test

The heat stability test was carried out according to the Japanese Industrial Standards (JIS) K6723 to determine a period of time (in minute) for which the specimen remained stable at 170±3 degrees C. This test was carried out as follows. The specimen was put in a test tube together with a test paper, congo red paper. The tube was sealed and then put in an oil bath at 170±3 degrees C. to measure a period of time which is necessary for the specimen to change, A time when a color of the congo red paper changed was regarded as the time when the specimen changed.

As apparent from Table 1, the present polyvinyl chloride resin compositions comprising di(2-ethylhexyl)terephthalate (DOTP) as a plasticizer and epoxidized soybean oil having the peroxide number of 5 or less were superior in heat, stability and processability, and showed the less elution and the less pH change. On the other hand, the composition of Comparative Example 1 comprising the epoxidized soybean oil in an amount less than the present lower limit was inferior in heat stability and processability. The compositions of Comparative Examples 3 to 6 where the peroxide number of epoxidized soybean oil was more than 5 showed the larger evaporation residues and the larger ultraviolet absorbences, compared to those in the compositions of Examples 1, 3, 5 and 6. This means that the former compositions had higher tendency to elution. Among these Examples and Comparative Examples, Example 3 and Comparative Example 3 showed the comparable levels of the evaporation resides and the ultraviolet absorbances, but the composition of Example 3 was superior in heat stability than that of Comparative Example 3. The compositions of Comparative Examples 7 to 14 comprising a plasticizer other than DOTP showed the larger pH change.

Example 8 and Comparative Examples 15 to 23

The components in the amounts (parts by weight) as shown in Table 2 were melt kneaded in a press kneader at approximately 160 degrees C. to prepare a polyvinyl chloride resin composition. The composition was put through rolls into a sheet. The sheet was formed into a predetermined size by a press machine to obtain a specimen. The specimen was subjected to the following GS-MS test. The results are as shown in Table 2.
GS-MS Test
(i) Extraction Test with Distilled Water
The specimen having a size of 65 mm×65 mm×2 mm and weight of approximately 10.00 g was washed with distilled water and dried at room temperature. This specimen was put in a 500 ml-volume glass container and closed, to which 300 ml of distilled water was then added, followed by shaking at 37 degrees C. for 5 hours. The distilled water was transferred to a 300 ml-volume volumetric flask, to which distilled water was further added to a total of just 300 ml to obtain a test solution. The sane procedures as described above were repeated without the specimen to obtain a blank test solution.

Each of the test solution and the blank test solution obtained above was evaporated to dryness using an evaporator to obtain a dried residue. The residue was dissolved in acetone and a total was adjusted to 10 ml in a volumetric flask. The solution was analyzed by a gas chromatography mass spectrometer (GC-MS apparatus) to determine an amount of the plasticizer (mg/ml) extracted into distilled water. Operation conditions areas fellows. A calibration curve was prepared using standard materials for DOTP, DOP, TOTM and DOA, ex Kanto Chemical Co., Inc., and a standard material for DINCH, ex BASF.
Operation Conditions:
Apparatus: GCMS-QP2010Plus (ex Shimadzu Corporation);
Column: DB-1 MS (ex Agilent Technologies, Inc.), 0.25 mm Φ×30 m with a membrane thickness of 0.25 μm;
Inlet temperature: 280 degrees C.;
Interface temperature: 280 degrees C.;
Carrier gas: helium (2 mL/min.)
Injected amount of a solution to be analyzed: 1 μL (using an auto-sampler);
Column temperature: 100 degrees C. (1 minute)-20 degrees C./min.-230 degrees C. (0 minute)-10 degrees C./min.-300 degrees C. (15 minutes).
(ii) Extraction Test with a 40 vol/vol % Ethanol Solution in Water
The same procedures as in test (i) above were repeated to determine an amount of a plasticizer (mg/ml) extracted into a 40 vol/vol % ethanol solution in water, except that the distilled water was replaced with the 40 vol/vol % ethanol solution in water. The ethanol solution was prepared from special grade ethanol, ex Kanto Chemical Co., and distilled water.

TABLE 2

|  |  | Example 8 | Comp. Ex. 15 | Comp. Ex. 16 | Comp. Ex. 17 | Comp. Ex. 18 | Comp. Ex. 19 | Comp. Ex. 20 | Comp. Ex. 21 | Comp. Ex. 22 | Comp. Ex. 23 |
|---|---|---|---|---|---|---|---|---|---|---|---|
| Composition | PVC | 100 | 100 | 100 | 100 | 100 | 100 | 100 | 100 | 100 | 100 |
|  | DOTP (molecular weight: 391) | 50 | 50 | 0 | 0 | 0 | 0 | 0 | 0 | 0 | 0 |
|  | DOP (molecular weight: 391) | 0 | 0 | 50 | 50 | 0 | 0 | 0 | 0 | 0 | 0 |
|  | TOTM (molecular weight: 547) | 0 | 0 | 0 | 0 | 50 | 50 | 0 | 0 | 0 | 0 |
|  | DINCH (molecular weight: 424) | 0 | 0 | 0 | 0 | 0 | 0 | 50 | 50 | 0 | 0 |
|  | DOA (molecular weight: 371) | 0 | 0 | 0 | 0 | 0 | 0 | 0 | 0 | 50 | 50 |
|  | Epoxidized soybean oil (peroxide number: 3) | 10 | 0 | 10 | 0 | 10 | 0 | 10 | 0 | 10 | 0 |
|  | Epoxidized soybean oil (peroxide number: 8) | 0 | 10 | 0 | 10 | 0 | 10 | 0 | 10 | 0 | 10 |
|  | Ca—Zn type composite stabilizer | 0.25 | 0.25 | 0.25 | 0.25 | 0.25 | 0.25 | 0.25 | 0.25 | 0.25 | 0.25 |
| Results of extraction tests | Distilled water, mg/ml | ND | ND | $1.20 \times 10^{-5}$ | $3.00 \times 10^{-5}$ | $9.60 \times 10^{-5}$ | $5.80 \times 10^{-7}$ | ND | ND | $9.40 \times 10^{-5}$ | $3.30 \times 10^{-6}$ |
|  | 40 vol/vol % Ethanol solution in water, mg/ml | $7.40 \times 10^{-7}$ | $3.20 \times 10^{-5}$ | $5.40 \times 10^{-3}$ | $9.60 \times 10^{-3}$ | $7.50 \times 10^{-5}$ | $2.10 \times 10^{-8}$ | $8.30 \times 10^{-5}$ | $2.10 \times 10^{-4}$ | $1.60 \times 10^{-2}$ | $5.60 \times 10^{-2}$ |

ND = Not detected

As apparent from Table 2, the composition of Example 8 comprising DOTP as a plasticizer and epoxidized soybean oil having the peroxide number of 5 or less showed the less elutions of the plasticizer into distilled water and into the aqueous ethanol solution, compared to those in the compositions of Comparative Examples 15 to 23 which met only one or neither of the aforesaid two requirements.

The invention claimed is:
1. A method for producing a medical instrument by forming a polyvinyl chloride resin composition which comprises 100 parts by weight of a polyvinyl chloride resin, 10 to 120 parts by weight of a plasticizer consisting essentially of di(2-ethylhexyl)terephthalate, and 0.5 to 20 parts by weight of epoxidized vegetable oil having a peroxide number of 5 or less; wherein plasticizers other than di(2- ethylhexyl) terephthalate are either not present in the composition or are present in the composition only in trace amounts.

2. The method according to claim 1, wherein the composition further comprises 0.05 to 10 parts by weight of silicone oil.

3. The method according to claim 1, wherein the instrument is a medical tube or a medical bag.

* * * * *